United States Patent [19]

Page et al.

[11] Patent Number: 5,208,323

[45] Date of Patent: May 4, 1993

[54] COUPLING OF AN ANTI-TUMOR TO AN ANTIBODY USING GLUTARALDEHYDE PREACTIVATED ANTI-TUMOR AGENT

[75] Inventors: Michel Page, Charlesbourg; Denis Thibeault, Ste-Foy, both of Canada

[73] Assignee: Universite Laval, Quebec, Canada

[21] Appl. No.: 819,669

[22] Filed: Jan. 13, 1992

Related U.S. Application Data

[63] Continuation of Ser. No. 391,928, Aug. 10, 1989, abandoned.

[51] Int. Cl.$^5$ .................. C07K 17/02; C07K 15/28; A61K 39/44; A61K 37/04
[52] U.S. Cl. .................. 530/391.9; 530/327; 530/345; 530/394; 530/395; 530/405; 530/406; 530/409; 530/410; 424/85.91; 514/2; 514/8; 514/12; 514/21; 536/6.4; 435/961
[58] Field of Search ............... 530/327, 345, 391.9, 530/394, 395, 406, 409, 410, 405; 424/85.91; 514/2, 8, 12, 21; 435/961; 436/548; 536/6.4

[56] References Cited

U.S. PATENT DOCUMENTS

| | | | |
|---|---|---|---|
| 4,263,279 | 4/1981 | Sela et al. | 424/85.91 |
| 4,625,019 | 11/1986 | Relyveld | 536/6.4 |
| 4,671,958 | 6/1987 | Rodwell et al. | 424/85.91 |
| 4,771,128 | 9/1988 | Ferris et al. | 530/391 |
| 4,843,147 | 6/1989 | Levy et al. | 530/391 |
| 4,886,780 | 12/1989 | Faulk | 514/8 |
| 5,087,616 | 2/1992 | Myers et al. | 514/21 |
| 5,108,987 | 4/1992 | Faulk | 514/8 |
| 5,120,525 | 6/1992 | Goldenberg | 424/1.1 |

OTHER PUBLICATIONS

"Table 1" sequence of Bombesin and Lys3 Bombesin.
Blair et al (1983) J. Immunol. Methods 59:129–143.
Coy et al (1988) J. Biol. Chem. 263(n):5056–5060.
Kennedy et al (1976) Clinica Chim. Acta 70:1–31.
Belles-Isles et al. "Anti-Oncofoetal Proteins for Targeting Cytotoxic Drugs", Int. J. Immunopharmac., vol. 3 (1981, Pergamon Press, Ltd.), pp. 97–102.
Bernier et al. "A Chlorambucil–Anti-CEA Conjugate Cytotoxid for Human Colon Adenocarcinoma Cells In Vitro", Br. J. Cancer, vol. 49 (1984, MacMillan Press, Ltd.), pp. 245–246.
Page et al. "Chemotherapy With Daunorubicin-Anti--CEA Conjugates in Human Colon Adenocarcinoma Grafted in Nude Mice", Seminars in Oncology, vol. 11, Suppl. 3 (Dec. 1984), pp. 308–310.
Pietersz, Geoffrey A. "The Linkage of Cytotoxic Drugs to Monoclonal Antibodies for the Treatment of Cancer", Bioconjugate Chemistry, vol. 1, No. (Mar.-/Apr. 1990), pp. 89–95.
Sinkule et al. "Monoclonal Antibody 44-3A6 Doxorubicin Immunoconjugates: Comparative in vitro Anti-tumor Efficacy of Different Conjugation Methods", Tumor Biol., vol. 12 (1991), pp. 198–206.
Belles-Isles et al. "In Vitro Activity of Daunomycin-Anti-Alphafoetoprotein Conjugate on Mouse Hepatoma Cells", Br. J. Cancer, vol. 41 (1980), pp. 841–842.

Primary Examiner—Christine M. Nucker
Assistant Examiner—Kay K. Kim
Attorney, Agent, or Firm—Cushman, Darby & Cushman

[57] ABSTRACT

The present invention relates to antitumor compounds of the formula I:

$$R-\overset{O}{\underset{\|}{C}}-(CH_2)_3-\overset{O}{\underset{\|}{C}}-M \qquad I$$

wherein M is selected from the group consisting of an hydrogen atom, a peptide residue, and a protein residue linked to the carbon atom via the amino residue of ε-lysine present therein which can be an antibody used to target the anti-tumor agent to the malignant cells, and R can be an antitumor agent such as daunorubicin, doxorubicin, or an epirublicin derivative.

6 Claims, 4 Drawing Sheets

COUPLING OF AN ANTI-TUMOR TO AN ANTIBODY USING GLUTARALDEHYDE PREACTIVATED ANTI-TUMOR AGENT

This is a continuation of application Ser. No. 07/391,928, filed on Aug. 10. 1989, which is abandoned.

BACKGROUND OF THE INVENTION

Chemotherapeutic agents current used for antitumor therapy are selected for their toxicity towards rapidly proliferating cells. Most of them cause undesirable systemic effects such as cardiac or renal toxicity, marrow aplasia, alopecia, nausea and vomiting. During the last few years, many authors have tried to eliminate these side effects by increasing the availability of the drug to the tumour site. Enzymes, radioisotopes, DNA, toxins, various macromolecules, and antibodies against fibrin or against tumour-specific surface antigens were bound to drugs in an attempt to increase the selectivity of the chemotherapeutic agents, or to decrease their toxic effects on normal cells (Rubens R. D., Lancet, 1, 1974, pp. 498-499; Gregoriadis G. et al., Res. Commun. Chem. Pathol. Pharm., 10, 1977, pp. 351-362).

The targeting of drugs to a tumour by antibodies to surface antigens may have considerable implications by increasing the therapeutic index.

It is recognized that the ideal antineoplastic drug would destroy cancer cells without adverse effects or toxicities on normal cells, but no such drug exists. However, despite the narrow therapeutic index of many drugs, treatment and even cure are possible in some patients.

Dactinomycin, doxorubicin and daunorubicin are all given rapidly intravenously and all cause tissue necrosis if extravasation occurs. When doxorubicin and daunorubicin are given rapidly intravenously, there is rapid dispersement throughout tissues and plasma. The $\neq t\frac{1}{2}$ is 30 min, with detectable plasma levels of doxorubicin up to 15 h. Both doxorubicin and daunorubicin are extensively metabolized by the liver, yielding active and inactive metabolites.

Dactinomycin, doxorubicin and daunorubicin have limited antitumor activity. Dactinomycin is effective in testicular carcinoma and sarcomas. Daunorubicin is effective in treating acute leukemia. In contrast, doxorubicin is one of the most active antineoplastic ever identified. In fact it is used to treat acute leukemia, Hodgkin's disease and non-Hodgkin's lymphomas, small cell and non-small cell lung cancer, cancers of the breast, ovaries, stomach, thyroid, and bladder, osteogenic and soft tissue sarcomas, and malignant melanoma. The side effects include nauseas, vomiting, alopecia, myelosuppression, and dose-dependent cardiotoxicity ($>550$ mg/m$^2$).

Relyveld, U.S. Pat. No. 4,625,019, describes an autopolymerized antitumor agent, that is, daunorubicin is brought in contact with a bifunctional crosslinking agent, such as glutaraldehyde. A form of polymeric product is obtained, which is insoluble in aqueous media but which, on being resuspended in an aqueous medium in the absence of glutaraldehyde, gradually releases the antitumor agent in a soluble form. This method mainly consist of mixing together daunorubicin, an antibody and glutaraldehyde, which can combine in three different ways. The conjugates obtained can be any of the followings:

1-33%: Antibody-glutaraldehyde-Daunorubicin
2-33%: Antibody-glutaraldehyde-Antibody
3-33%: Daunorubicin-glutaraldehyde-Daunorubicin and which only the Antibody-glutaraldehyde-Daunorubicin conjugate is active. Furthermore, these three possible conjugates can be linked together by the excess glutaraldehyde in solution to form an agglomerate, which makes it difficult to isolate the active conjugate. This is the reason why we refer to an autopolymerized antitumor agent in this patent.

This method is not readily reproducible and give an unstable conjugate product. Unfortunately, this autopolymerized antitumor agent has the disadvantage of being insoluble in water and thus looses its specific activity against tumor cells. This insoluble product can not be used intravenously for a systemic treatment since it is taken up by phagocytic cells such as monocytes, marcrophage or cells. This product is not very stable and do not have a very long shelf life.

The problems posed by the administration of antitumor agents or cytostatic agents are made particularly difficult by the nature of the illness and very high toxicity of the active products.

It would be highly desirable if the efficiency of the use of antitumor agents could be improved so as to allow their gradual release in the organism, while clearly improving their efficiency and the patient's comfort. It would also be highly desirable, if there could be such an antitumor agent which would be easily produce, substantially pure, which would also not have a tendency to polymerized and hence have a long shelf life.

SUMMARY OF THE INVENTION

Surprisingly and in accordance with the present invention, there is provided antitumor agents overcome the drawback of the prior art. The already reported techniques for coupling anthracycline drugs to antibody either cause polymerization or yield a product which is considerably less active than the free drug. Using the method of the present invention, a wide variety of monoclonal antibodies specific for various tumors are conjugated to other carriers that could be used for drug targeting.

In accordance with the present invention, there is provided novel compounds of the formula I:

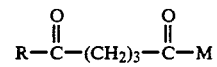

$$R-\overset{O}{\underset{\|}{C}}-(CH_2)_3-\overset{O}{\underset{\|}{C}}-M \qquad I$$

wherein,

M is selected from the following group consisting of an hydrogen atom, a peptide residue and a protein residue linked to the carbon atom via the amino residue of ε-lysine present therein, and R is an antitumor agent residue such as daunorubicin, doxorubicin, or epirubicin.

When M is a protein, it can be an antibody which is used to target the antitumor agent to the malignant cells and thereby improving the conditions of such anti-cancer treatments.

The compounds of the present invention are easily produced and are devoid of significant polymerization since they are substantially pure. The compounds of the present invention have the ability to provide the full pharmacological activity of the antitumor agent without the disadvantage normally associated with said antitumor agent. The improved coupling procedure of the present invention involved in the production of these compounds of formula I is readily reproducible and the resulting compounds are substantially stable at 25° C.

Other advantages of the present invention will be readily illustrated by referring to the following description.

IN THE DRAWINGS

DETAILED DESCRIPTION OF THE INVENTION

Figure 1:
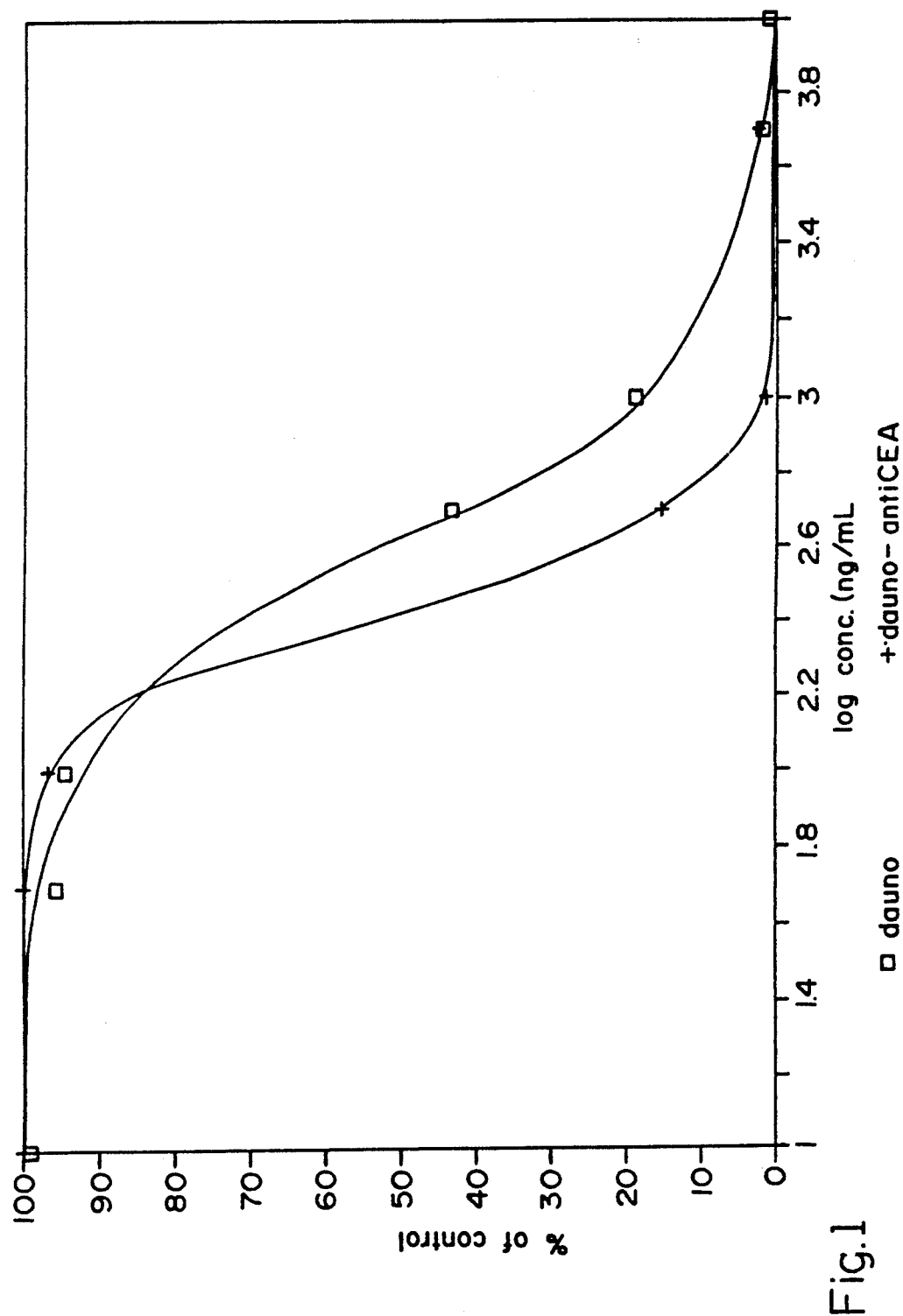
FIG. 1 shows the Cytotoxicity of Equimolar Concentrations of Free or Monoclonal AntiCEA Bound Daunorubicin on Human Color Adenocarcinoma Cells (LoVo).

The compounds of the present invention correspond to the general formula I:

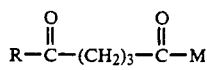

wherein R and M are as defined previously.

The products of the present invention are prepared as follows:

An antitumor agent R is first reached with an excess of glutaraldehyde, which gives an intermediate R-glutaraldehyde of formula (I), wherein M is an hydrogen atom. This intermediate reaction product has a terminal aldehyde group.

The intermediate reaction product is extracted with a solvent such as dichloromethane to yield a purified activated R-glutaraldehyde having a terminal aldehyde group. This activated R-glutaraldehyde product is then dried on Na-sulfate and dissolved in a solvent such as dimethylsulfoxide (DMSO) and then is reacted with an ϵ-lysine containing protein or peptide to yield the final conjugate R-glutaraldehyde-M. This conjugate is finally obtained by a simple gel filtration.

Results obtained with activated daunorubicin using this new procedure show that the pharmacological activity of the drug could be saved while limiting the undesirable polymerization of the antibody normally encountered with bivalent coupling agents. This procedure is easy and reproducible and reagents are readily available commercially. The activation of the drug can be accomplished in less than 2 hours and the activated drug remains active for a week at room temperature.

It has also been found that the activated drug can retain its activity for many months it stored in liquid nitrogen.

All the improvements of the R-glutaraldehyde-M conjugate of the present invention can be seen from the following reaction schemes. The method of the present invention is readily reproducible and gives a R-glutaraldehyde-M conjugate, which does not have a tendency to polymerize.

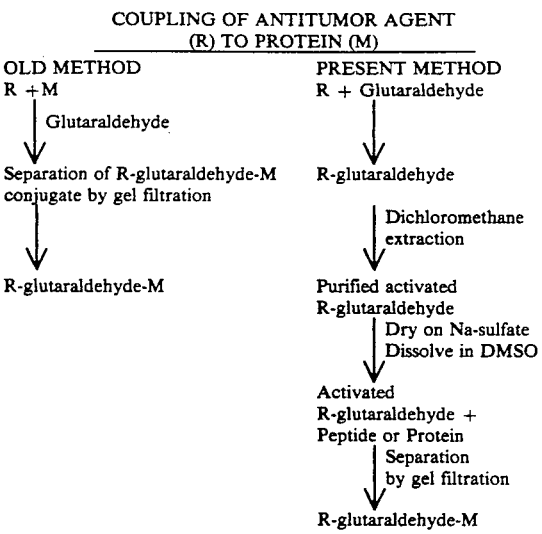

Cell Lines

The cell lines were only used as targets to show that the conjugate can be directed to the desired sites. As cell lines there may be used: human embryonic intestine cells (CCL-6), human amnion cells (CCL-25), human osteosarcoma cells (CRL-1427), human ovarian carcinoma (CRL-1572), human hepatoma cells (HS-703-T), Mouse melanoma (CRL-6323) and LoVo human adenocarcinoma cells (CCL-229). These cell lines are readily available from the American Type Culture Collection under the numbers shown in brackets, except for the human hepatoma (HS-703-T) which can be obtained from Dr. Williams C. Parks at Michigan State University, East Lansing, Mich., U.S.A.

The LoVo cells produce carcinoembryonic antigen in culture. The human ovarian carcinoma cells produce alphafoetoprotein. All cell lines are routinely cultured in RPMI-1640 ® medium supplemented with 10% foetal bovine serum and 100 ug per ml of streptomycin and 100 ug per ml of penicillin.

Antibody and Peptide

The antibodies and peptides were only used in order to direct the conjugates to the desired cell lines used. The antibodies were obtained through standard monoclonal antibody production procedures using the above-mentioned cells lines. As antibodies there may be used: anti-carcinoembryonic monoclonal, anti-carcinoembryonic polyclonal antibody, anti-alphafetoprotein monoclonal, anti-alphafetoprotein polyclonal antibody, anti-embryonic pre-albumin monoclonal antibody. As a peptide there may be used: human transferrin and lys-bombesin.

'In vitro' Cytotoxicity

In order to evaluate the efficiency of the compounds of formula (I), the following procedure is used and other methods of in vitro cytotoxicity could have been used.

The conjugate solution is adjusted to 2% bovine serum albumin in 0.05 M ammonium acetate buffer. The solution is then freeze dried and gamma radiated with 16,000 rads. Before the assay, the dry conjugate is taken up in Dulbecco ® phosphate buffer saline and added at various concentrations to culture medium.

The cytotoxic activity of daunorubicin and antiCEA conjugate on the various cell lines is evaluated by inhibition of colony formation as described in Emond et al., Anthracyclines, 1983, Ed. G. Mathè, Masson Publish N.Y., U.S.A., 105. Briefly, 2,500 cells are added to 1 ml of RPMI 1640® medium supplemented with 10% foetal bovine serum in 24 well plates. Cells re allowed to attach for 24 hours, medium is removed and replaced by various test compounds diluted in growth medium. The tested drugs are incubated with the cells for four days in complete growth medium. Each assay is performed in quadruplicate.

After the growth period, medium is decanted, colonies are fixed with formol and stained with crystal violet as reported in Belles-Isles et al., Brit. J. Cancer, 1980, 41, 840.

Following the procedures of the present invention, the following compounds have been obtained:

| R | M |
|---|---|
| daunorubicin | hydrogen |
| doxorubicin | hydrogen |
| epirubicin | hydrogen |
| daunorubicin | antiCEA |
| doxorubicin | antiCEA |
| epirubicin | antiCEA |
| daunorubicin | antiAFP |
| doxorubicin | antiAFP |
| epirubicin | antiAFP |
| daunorubicin | antiCA-125 |
| doxorubicin | antiCA-125 |
| epirubicin | antiCA-125 |
| daunorubicin | lys-bombesin |
| doxorubicin | lys-bombesin |
| epirubicin | lys-bombesin |
| daunorubicin | antiEPA |
| doxorubicin | antiEPA |
| epirubicin | antiEPA |

Cytotoxicity of conjugates

Figure 2:
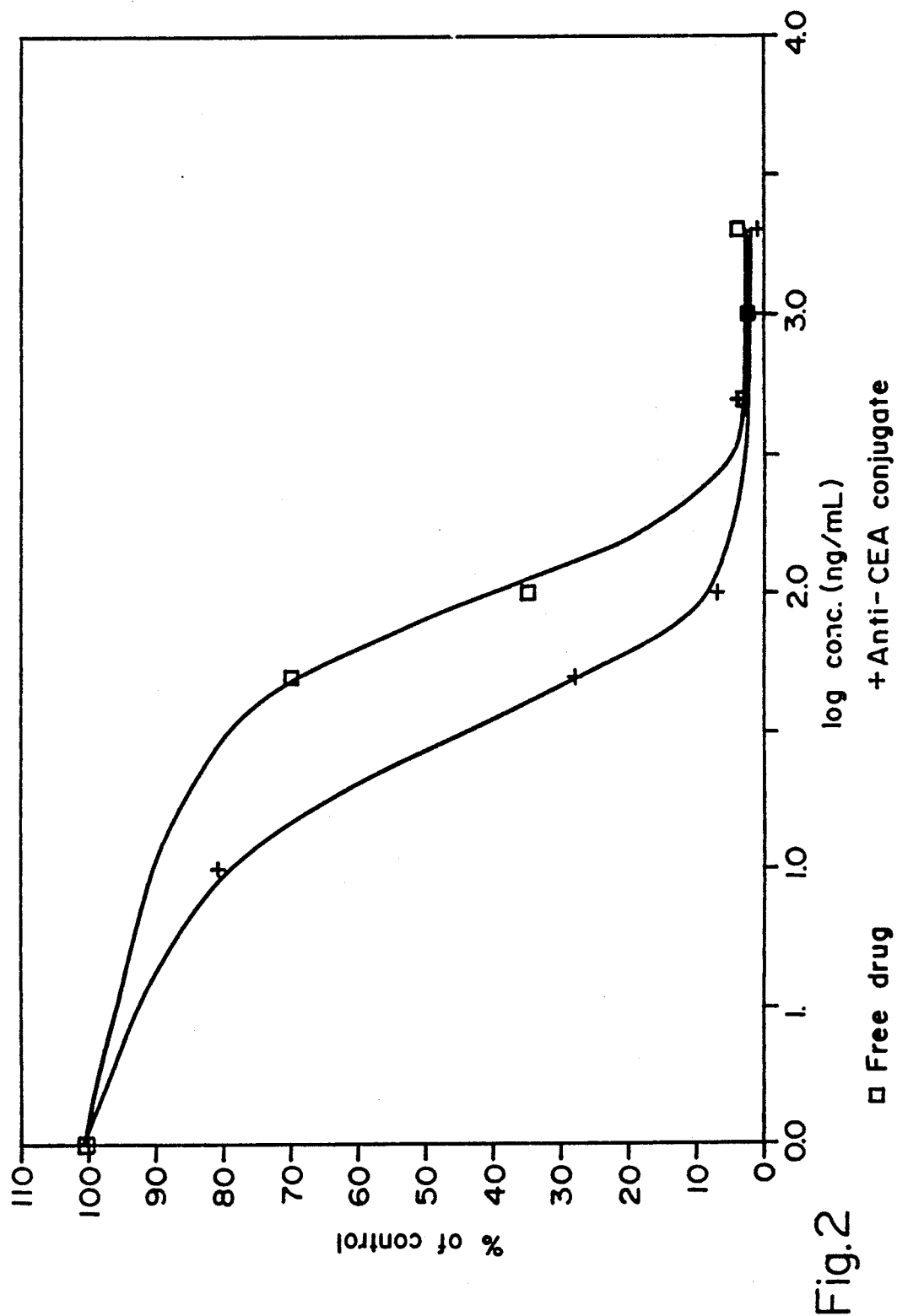
FIG. 2 shows the Cytotoxicity of Equipmolar Concentrations of Free or Monoclonal AntiCEA Bound Daunorubicin on Human MG-3 Osteosarcoma Cells.

Results obtained by inhibition of colony formation on the cytotoxicity of free of antiCEA bound daunorubicin are shown on FIGS. 1 to 4. For any cell line used, we find a dose-response relationship is determined. The cytotoxicity of antiCEA conjugate for LoVo cells is 250 ng/ml as compared to 400 ng/ml for the free drug (FIG. 1); the cytotoxicity of antiCEA conjugate for human osteosarcoma (CRL-1427) cells is significantly higher than the one of the free drug (FIG. 2).

Figure 3:
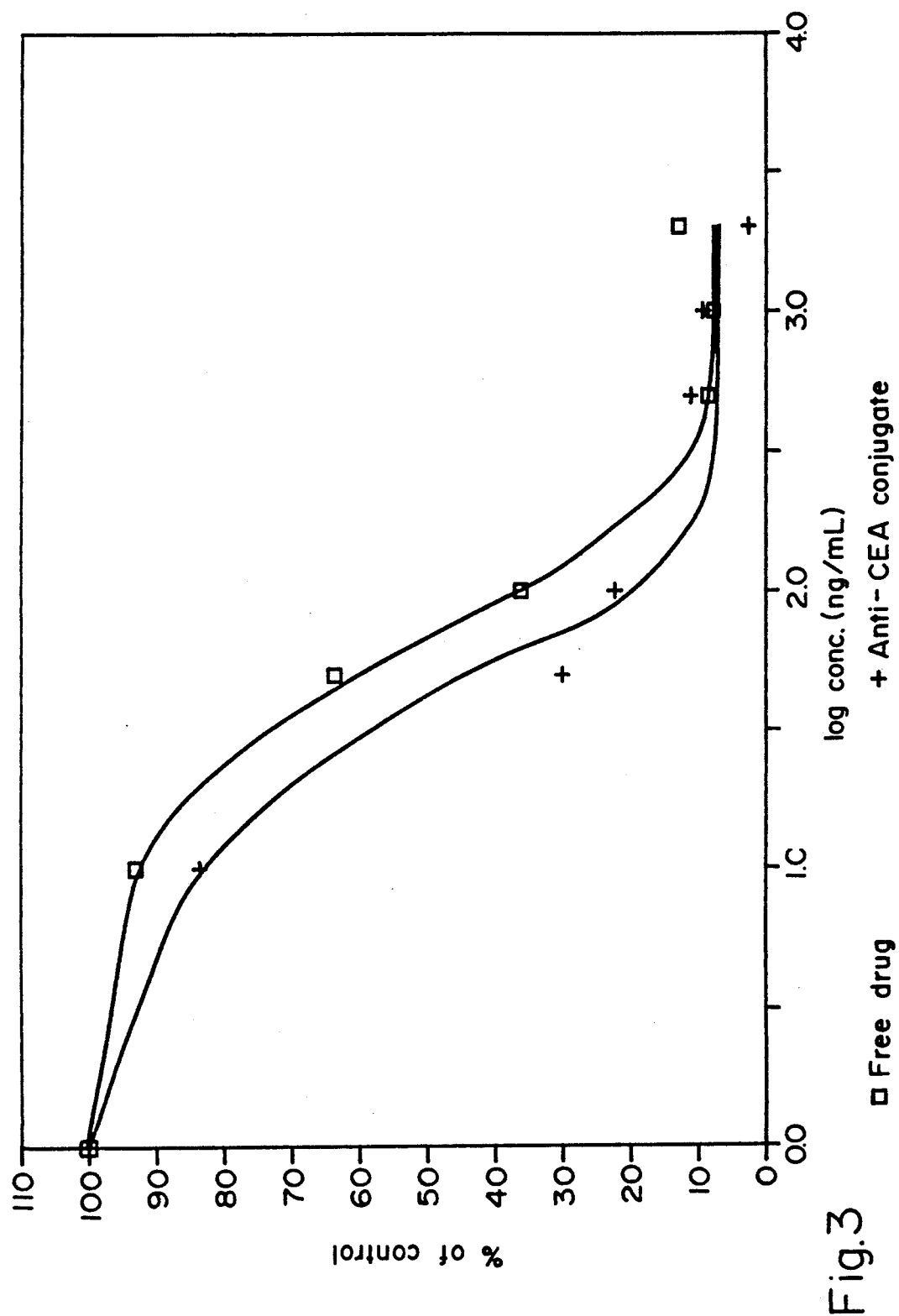
FIG. 3 shows the Cytotoxicity of Equimolar Concentrations of Free or Monoclonal AntiCEA Bound Daunorubicin on Human Amnion Cells.
Figure 4:
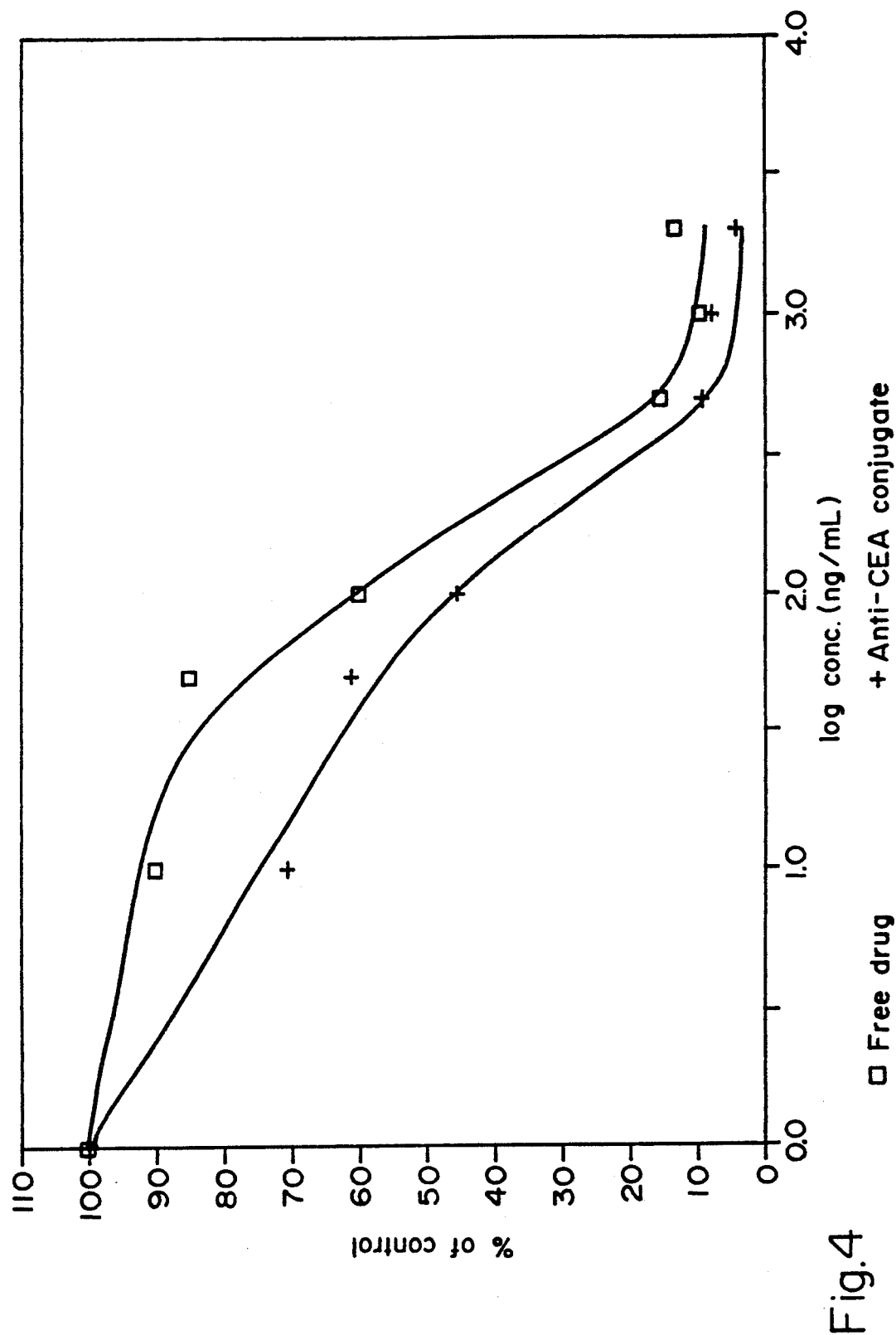
FIG. 4 shows the Cytotoxicity of Equimolar Concentrations of Free or Monoclonal AntiCEA Bound Daunorubicin on Human Embryonic Intestine Cells (CCL-6).

The conjugate is more cytotoxic for normal human amnion cells and human embryonic intestine (CCL-6) than the free drug (FIGS. 3 and 4).

The $LD_{50}$ (lethal dose to kill 50% of the malignant cells) of free and bound antitumor agent for the various cell lines is reported in Table 1 below.

TABLE 1

Cytotoxicity ($LD_{50}$:mg/ml) of Free and Bound Daunorubicin For the Various Cell Lines

| CELL LINES | FREE DRUG daunorubicin | CONJUGATE | % $LD_{50}$ decrease |
|---|---|---|---|
| | | Anti-CEA-daunorubicin | |
| human colon adenocarcinoma | 400 | 250 | 37 |
| human osteosarcoma | 75 | 24 | 68 |
| human amnion | 77 | 29 | 62 |
| human embryonic intestine | 142 | 83 | 42 |
| | | Anti-EPA-daunorubicin | |
| human osteosarcoma | 160 | 91 | 43 |

TABLE 1-continued

Cytotoxicity ($LD_{50}$:mg/ml) of Free and Bound Daunorubicin For the Various Cell Lines

| CELL LINES | FREE DRUG daunorubicin | CONJUGATE | % $LD_{50}$ decrease |
|---|---|---|---|
| | | Anti-alpha-foetoprotein-daunorubicin | |
| human amnion | 57 | 49 | 14 |
| human hepatoma | 41 | 31 | 24 |
| human osteosarcoma | 30 | 12 | 60 |

It can be seen that the dosage required to inhibit 50% of the malignant cells for the compounds of the present invention is much lower than for the free drug itself. The lower the $LD_{50}$ the better the drug targetting is and hence less sides effects are observed. The $LD_{50}$ % decrease is found between 14% to 68% depending on the drug or the cell line used. Compounds with such an ability to target antitumor agents without substantially lowering their pharmaceutical activity were long waited for.

The method of the present invention for coupling an antitumor agent to an antibody provides molar ratios of anti-tumor to antibody varying from 0.5:1 to 13:1 as desired. The preferred molar ratios for coupling anti-tumor agent to antibody being 5:1 to 7:1.

The glutaraldehyde being used is a 25% aqueous solution of glutaraldehyde in a stoichiometric amount.

The present invention will be more readily understood by referring to the following Examples which are given to illustrate the invention rather than to limit its scope.

EXAMPLE 1

A-Glutaraldehyde Activated Daunorubicin

One mg of daunorubicin hydrochloride is dissolved in 4 ml of 0.05 M phosphate buffer at pH 7.5 and 60 ul of 25% glutaraldehyde is added (grade II, Sigma Chemicals, St. Louis, USA). The mixture is stirred for 15 minutes at room temperature and 1 ml of distilled water is added. The mixture is extracted twice with 5 ml of dichloromethane; the organic phases are pooled and treated four times with an equal volume of 5% $NaHCO_3$ solution containing 15% glycine. The organic phase is dried with anhydrous sodium sulphate, filtered, and the solvent is evaporated under a stream of nitrogen at room temperature. The dried product is taken in a minimum volume of dimethylsulfoxide (DMSO).

The coefficient of extinction is $E_{495}1\% = 176$ in 10% dimethylsulfoxide in 0.05 M phosphate buffer at pH 7.2 for the activated derivative.

B-Antibody Purification

Monoclonal antiCEA 341-46-36 antigen is purified from mouse ascitic fluid by precipitation with 50% saturated ammonium sulphate. The antibody precipitate is dissolved in the original volume of phosphate buffer at pH 7.2 and dialyzed for 24 hours at 4° C. against Dulbecco® phosphate buffer saline. The antibody concentration is then measured with the Lowry method (Tsukada, Kato, Umemoto, Takeda, Hara and Hirai, H. J. Nat. Cancer Inst. 1984, 73, 721).

C-Conjugation Procedure

The glutaraldehyde activated daunorubicin derivative is dissolved in 100 ul of dimethylsulfoxide and added with stirring to 500 ug of monoclonal antiCEA antibody dissolved in 400 ul of phosphate buffer. The reaction mixture is incubated for 60 minutes at 37° C. and the protein conjugate is separated on Sephadex G-25® on a PD-10® column (Pharmacia, Canada), equilibrated with 0.05 M ammonium acetate at pH 6.5 containing 0.3 mM glycine. The conjugate appears in the void volume of the column. The conjugation ratio is determined by spectrophotometry taking an $E_{495}{}^{1\%}=176$ for daunorubicin and $^{1\%}E_{280}=4.5$ for monoclonal antibody.

There is obtained the Daunorubicin-Glutaraldehyde-AntiCEA monoclonal antibody conjugate.

EXAMPLE II

Proceding as in example I but using antiAFP antibody instead of the antiCEA monoclonal antibody in step B, there is obtained antiAFP-daunorubicin conjugate.

EXAMPLE III

Proceding as in example I but using antiCA-125 antibody instead of the antiCEA monoclonal antibody in step B, there is obtained antiCA-125-daunorubicin conjugate.

EXAMPLE IV

Proceding as in example I but using antiEPA antibody instead of the antiCEA monoclonal antibody in step B, there is obtained antiEPA-daunorubicin conjugate.

EXAMPLE V

Proceding as in example I but using lys-bombesin antibody instead of the antiCEA monoclonal antibody in step B, there is obtained lys-bombesin-daunorubicin conjugate.

EXAMPLE VI

Proceding as in example I but using doxorubicin instead of daunorubicin in step B, there is obtained antiCEA-doxorubicin conjugate.

EXAMPLE VII

Proceding as in example II but using doxorubicin instead of daunorubicin in step B, there is obtained antiAFP-doxorubicin conjugate.

EXAMPLE VIII

Proceding as in example III but using doxorubicin instead of daunorubicin in step B, there is obtained antiCA-125-doxorubicin conjugate.

EXAMPLE IX

Proceding as in example IV but using doxorubicin instead of daunorubicin in step B, there is obtained antiEPA-doxorubicin conjugate.

EXAMPLE X

Proceding as in example V but using doxorubicin instead of daunorubicin in step B, there is obtained lys-bombesin-doxorubicin conjugate.

EXAMPLE XI

Proceding as in example I but using epirubicin instead of daunorubicin in step B, there is obtained antiCEA-epirubicin conjugate.

EXAMPLE XII

Proceding as in example II but using epirubicin instead of daunorubicin in step B, there is obtained antiAFP-epirubicin conjugate.

EXAMPLE XIII

Proceding as in example III but using epirubicin instead of daunorubicin in step B, there is obtained antiCA-125-epirubicin conjugate.

EXAMPLE XIV

Proceding as in example IV but using epirubicin instead of daunorubicin in step B, there is obtained antiEPA-epirubicin conjugate.

EXAMPLE XV

Proceding as in example V but using epirubicin instead of daunorubicin in step B, there is obtained lys-bombesin-epirubicin conjugate.

I claim:

1. A method of preparing compounds of formula I

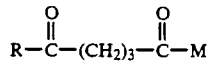

$$R-\overset{O}{\underset{\|}{C}}-(CH_2)_3-\overset{O}{\underset{\|}{C}}-M \qquad I$$

wherein M is selected from the group consisting of a peptide residue, and a protein residue linked to the carbon atom via an amino residue of ε-lysine present therein, and wherein R represents an anti-tumor agent residue, which comprises the steps of:

a reacting said antitumor agent with glutaraldehyde;
b purifying the activated product by extraction with dichloromethane; and
c reacting the drug-glutaraldehyde complex of step a) with a peptide or a protein M.

2. The method according to claim 1, wherein said antitumor agent is daunorubicin.

3. The method according to claim 1, wherein said antitumor agent is doxorubicin.

4. The method according to claim 1 wherein said antitumor agent is epirubicin.

5. The method according to claim 1, wherein said compound of formula I is antiCEA monoclonal antibody-daunorubicin conjugate.

6. The method according to claim 11, wherein M is a peptide selected from the group consisting of anti-carcinoembryonic monoclonal, anti-carcinoembryonic polyclonal antibody, anti-alphafetoprotein monoclonal, anti-alphafetoprotein polyclonal antibody, anti-embryonic pre-albumin monoclonal antibody, human transferrin and Lys3-bombesin.

* * * * *